US012636053B2

(12) United States Patent
Dacosta et al.

(10) Patent No.: US 12,636,053 B2
(45) Date of Patent: May 26, 2026

(54) BONE FIXATION PLATES AND ALIGNMENT GUIDES

(71) Applicant: Paragon 28, Inc., Englewood, CO (US)

(72) Inventors: Albert Dacosta, Lone Pine, CO (US);
Tristan Collette, Denver, CO (US);
Richard David Hunt, Arvada, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 18/672,694

(22) Filed: May 23, 2024

(65) Prior Publication Data

US 2024/0307100 A1 Sep. 19, 2024

Related U.S. Application Data

(63) Continuation of application No. PCT/US2022/080294, filed on Nov. 22, 2022.

(Continued)

(51) Int. Cl.
*A61B 17/80* (2006.01)
*A61B 17/17* (2006.01)
(Continued)

(52) U.S. Cl.
CPC ........ *A61B 17/808* (2013.01); *A61B 17/1725* (2013.01); *A61B 17/1775* (2016.11);
(Continued)

(58) Field of Classification Search
CPC ............ A61B 17/1725; A61B 17/1728; A61B 17/1775; A61B 17/8061; A61B 17/808;
(Continued)

(56) References Cited

U.S. PATENT DOCUMENTS 9,421,103 B2 * 8/2016 Jeng .................. A61B 17/1728
9,918,762 B2 * 3/2018 Federspiel ......... A61B 17/8085
(Continued)

FOREIGN PATENT DOCUMENTS

WO 2020014418 1/2020
WO 2020168058 8/2020

OTHER PUBLICATIONS

International Search Report and Written Opinion of the International Searching Authority for PCT/US2022/080294 dated Feb. 21, 2023, 10 pages.

(Continued)

*Primary Examiner* — Larry E Waggle, Jr.
(74) *Attorney, Agent, or Firm* — Heslin Rothenberg Farley & Mesiti P.C.; Jacquelyn A. Graff, Esq.

(57) ABSTRACT

A bone plate alignment system includes an alignment guide and a bone plate. The alignment guide includes a body portion, a first arm extending from a first side of the body portion, and a second arm extending from a second side of the body portion. The first and second arms extend from the body portion at a substantially oblique angle relative to one another. The bone plate includes an upper portion having at least one opening configured to receive at least one fastener to facilitate coupling with a first bone, a lower portion having at least one opening configured to receive at least one fastener to facilitate coupling with a second bone, and an intermediate portion disposed between the upper and lower portions, wherein the intermediate portion is configured to be disposed substantially adjacent both the first bone and the second bone.

20 Claims, 8 Drawing Sheets

Related U.S. Application Data

(60) Provisional application No. 63/264,477, filed on Nov. 23, 2021.

(51) Int. Cl.
A61B 17/90 (2006.01)
A61F 2/46 (2006.01)
*A61B 17/68* (2006.01)

(52) U.S. Cl.
CPC .......... *A61B 17/8061* (2013.01); *A61B 17/90* (2021.08); *A61F 2/4606* (2013.01); *A61B 2017/681* (2013.01); *A61F 2002/4687* (2013.01)

(58) Field of Classification Search
CPC .. A61B 17/8085; A61B 17/8872; A61B 17/90
See application file for complete search history.

(56) References Cited

U.S. PATENT DOCUMENTS

| | | | |
|---|---|---|---|
| 11,622,778 B2* | 4/2023 | Leither | A61B 17/1728 606/96 |
| 2013/0331947 A1 | 12/2013 | Surma et al. | |
| 2014/0107798 A1 | 4/2014 | Jeng et al. | |
| 2014/0180348 A1* | 6/2014 | Thoren | A61B 17/17 606/86 R |
| 2015/0359580 A1 | 12/2015 | Dacosta et al. | |
| 2018/0280069 A1 | 10/2018 | Barmes et al. | |
| 2019/0015140 A1 | 1/2019 | Dacosta | |
| 2020/0015868 A1* | 1/2020 | Dacosta | A61B 17/1728 |
| 2021/0085378 A1 | 3/2021 | Dacosta | |

OTHER PUBLICATIONS

International Preliminary Report on Patentability for International Application No. PCT/US2022/080294 dated May 2, 2024, 6 pages, International Bureau of WIPO.

* cited by examiner

300

400

410

412

414

420

422

436

428

430

432

434

400

412

410

414

420

422

428

436

430

434

432

BONE FIXATION PLATES AND ALIGNMENT GUIDES

CROSS-REFERENCE TO RELATED APPLICATIONS

This application is a bypass continuation of PCT Application No. PCT/US2022/080294, filed Nov. 22, 2022, and entitled "Bone Fixation Plates and Alignment Guides," which claims priority benefit under 35 U.S.C. § 119(e) of U.S. Provisional Application No. 63/264,477 filed Nov. 23, 2021, and entitled "Bone Fixation Plates and Alignment Guides," which are incorporated herein by reference in their entirety.

TECHNICAL FIELD

The present disclosure relates to implantable medical devices. The present disclosure relates to podiatric and orthopedic implants and procedures related the foot/ankle and/or procedures incorporating surrounding bones/soft tissue. More specifically, but not exclusively, the present disclosure relates to bone plates and associated instrumentation and methods for fixation of the ankle joint.

BACKGROUND OF THE INVENTION

Many currently available devices and systems for incorporation in procedures involving the foot/ankle do not completely address the needs of patients. Additionally, many currently available devices and systems for incorporation in procedures involving the foot/ankle fail to account for properties of joint anatomy and associated mechanical and kinematic movement patterns/capabilities.

SUMMARY OF THE INVENTION

The present disclosure is directed toward implants for fusion of bones of the foot and/or ankle. More specifically, the present disclosure is directed toward bone plates for fusion of the ankle joint.

A bone plate alignment system includes an alignment guide and a bone plate. The alignment guide includes a body portion, a first arm extending from a first side of the body portion, and a second arm extending from a second side of the body portion. The first and second arms extend from the body portion at a substantially oblique angle relative to one another. The bone plate includes an upper portion having at least one opening configured to receive at least one fastener to facilitate coupling with a first bone, a lower portion having at least one opening configured to receive at least one fastener to facilitate coupling with a second bone, and an intermediate portion disposed between the upper and lower portions, wherein the intermediate portion is configured to be disposed substantially adjacent both the first bone and the second bone.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION OF THE INVENTION

Figure 1:
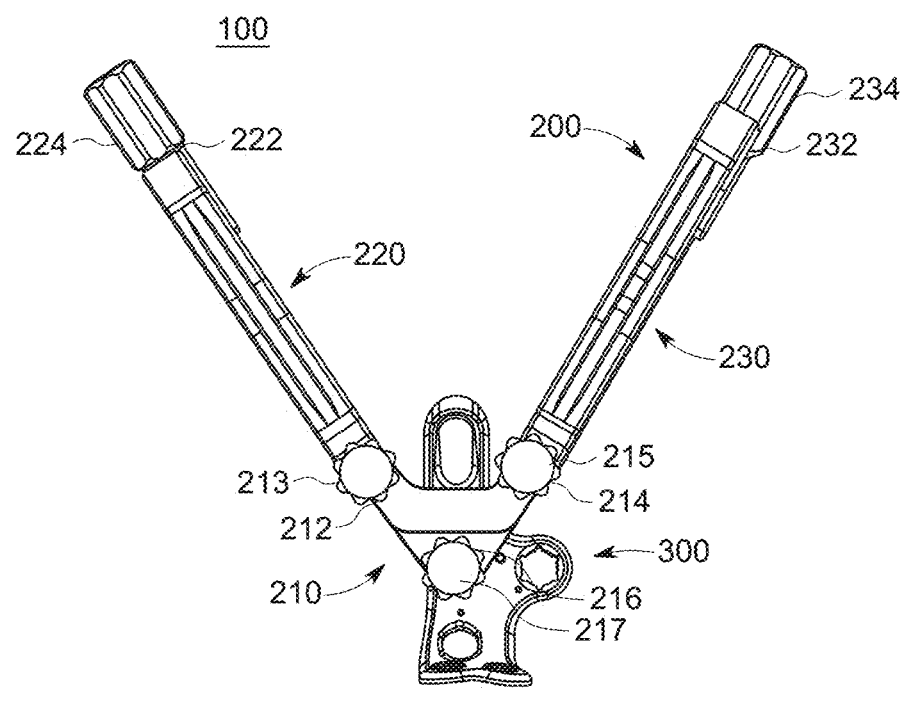
FIG. 1 is a front view of a system for aligning and implanting a bone plate, in accordance with the present disclosure.
Figure 2:
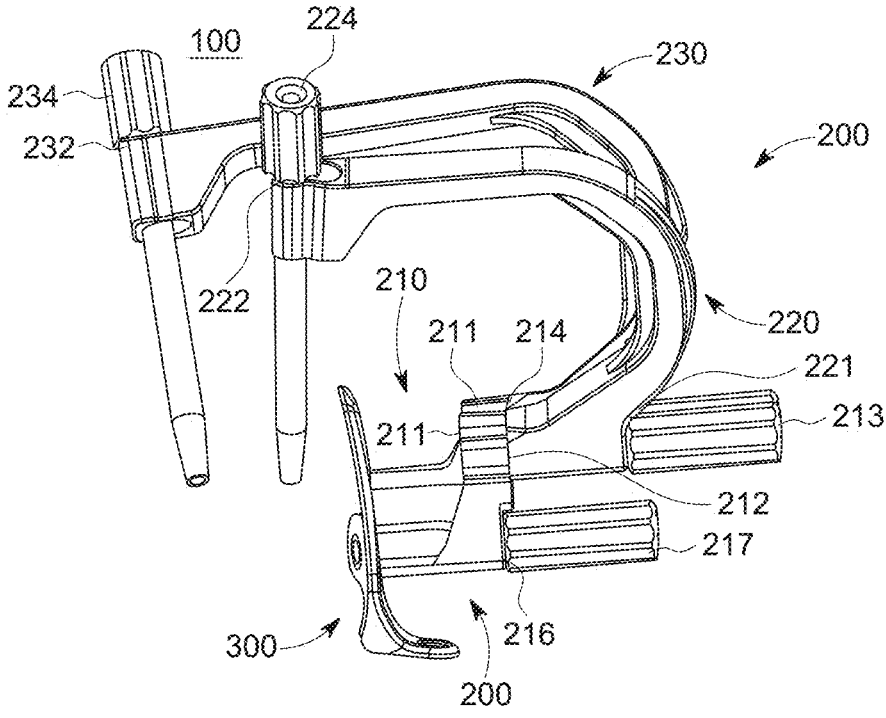
FIG. 2 is a side perspective view of the system for aligning and implanting the bone plate of FIG. 1, in accordance with the present disclosure.
Figure 3:
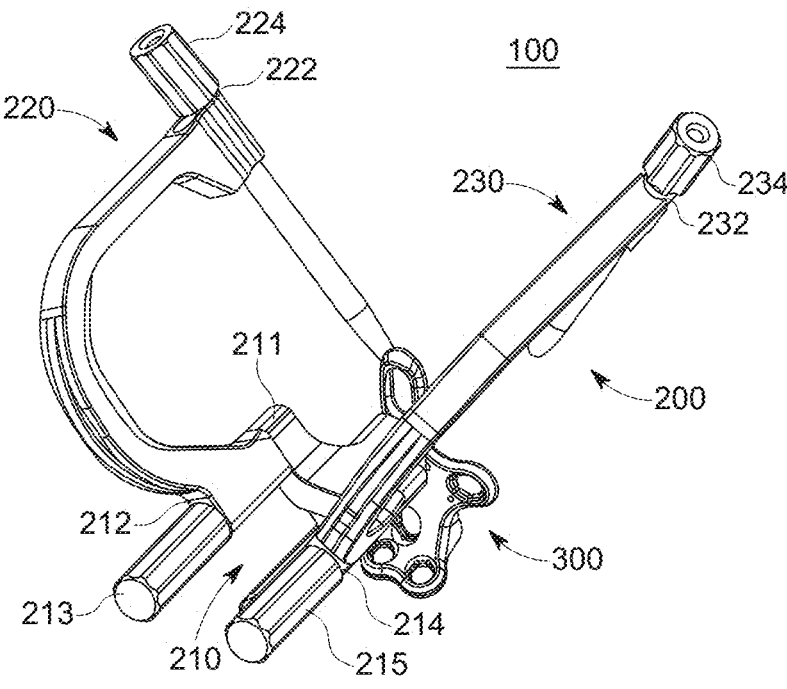
FIG. 3 is an elevated perspective view of the system for aligning and implanting the bone plate of FIG. 1, in accordance with the present disclosure.
Figure 4:
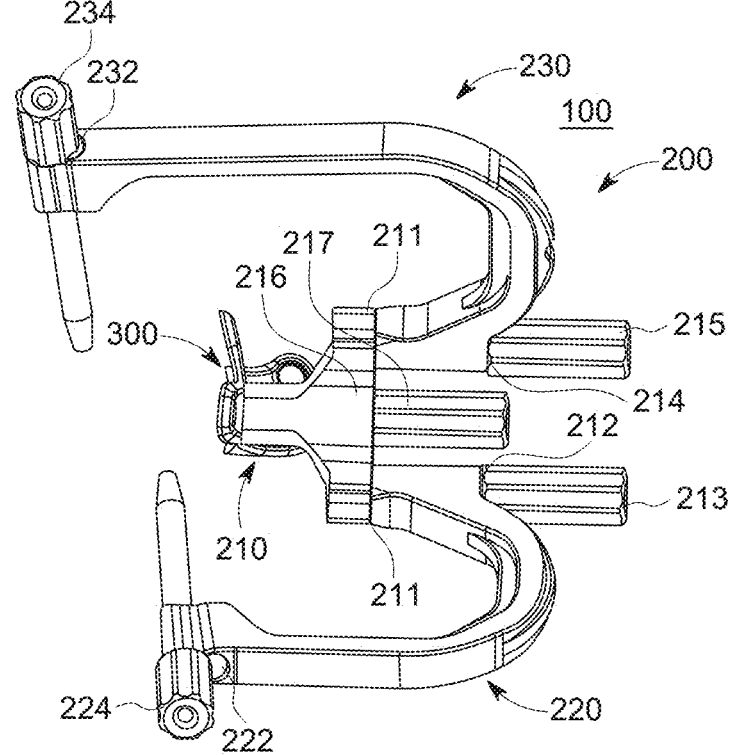
FIG. 4 is a top view of the system for aligning and implanting the bone plate of FIG. 1, in accordance with the present disclosure.

In this detailed description and the following claims, the words proximal, distal, anterior, or plantar, posterior, or dorsal, medial, lateral, superior, and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation, and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

Referring to the drawings, a system for aligning and implanting a bone plate is shown as well as various fixation implants (referred to hereinafter as "bone plates" or "plates") that may be implemented in conjunction with said system. It should be noted that the components shown and described herein may not include all components in such a system (for example, such a system may include various instrumentation, fasteners, and other components commonly associated with orthopedic procedures and implants). The bone plates shown in FIGS. 1-4 and 7-16 may be implanted in the foot and/or ankle region of a patient in order to provide fixation and/or fusion of one or more joints. For example, an upper portion of the bone plates may be configured to receive one or more fasteners through one or more openings to couple the upper portion of the bone plate with a first bone. In some aspects, the first bone with which the upper portion of the bone plate may couple may be the tibia (or more specifically, a distal portion of the tibia. Further to the previous example, the bone plates may also include a lower portion thereof having one or more openings configured to receive one or more fasteners to couple the lower portion of the bone plate with a second bone. In some aspects, the lower portion of the bone plate may have a smaller footprint and/or fewer openings that the upper portion of the bone plate. The lower portion of the bone plate may be configured to couple with a bone adjacent the distal tibia, for example the talus of a patient. The bone plate also includes a central portion of the bone plate disposed substantially between the upper portion and lower portion of the bone plate. In some aspects, the central portion may include one or more openings configured to receive temporary intraoperative fixation elements (e.g., k-wire, etc.). The central portion may also include an angled portion or be angled entirely, with said angulation relative to the upper and lower portions of the bone plate. For example, the upper and lower portions of the bone plate may have surfaces in planes that are substantially orthogonal to one another, with the central portion including a curvature and/or orthogonal angle.

The bone plates shown and described herein may also be a component of an implant system. For example, an implant system may include (but is not limited to) fasteners, instrumentation, and additional implant components. In some aspects, said additional implant components may include cage implants or other implants configured to fill a void in a bone and/or joint space. The bone plates shown herein may be implanted adjected to such a cage, for example with the cage implanted between the tibia and the talus and the bone plate positioned straddling, spanning, or otherwise substantially adjacent such a cage. In some aspects the cages may have various geometries including but not limited to sphere, cube, ovoid, or other alternate geometries.

Referring now to FIGS. 1-4, a system 100 for aligning and implanting a bone plate is shown, according to an exemplary embodiment. The system 100 is shown to include an alignment guide 200 and a bone plate (referred to hereinafter as the "plate") 300. The alignment guide 200 is shown to be releasably couplable with the plate 300, and furthermore may be releasably coupled with one or more portions of the anatomy of a patient (e.g., releasably coupled via k-wires, stabilization wires, etc. to the tibia or other anatomy of the patient). It should be noted that the system 100 as shown and described herein may include additional components. For example, the system 100 may be provided (e.g., sold, packaged, implemented by a physician, etc.) to a healthcare professional along with additional components such as instrumentation specific to the system and/or common to orthopedic procedures, fasteners and/or other fixation components (e.g., screws, k-wires, etc.), or other additional components. It should also be understood that the system 100 may be implemented in conjunction with various bone plates or other components from those shown and described herein, for example with alternate bone plates. Similarly, it should be noted that the bone plates shown and described herein (e.g., plate 300) may be implemented in conjunction with systems, alignment guides, and instrumentation other than that which is shown and described herein.

The alignment guide 200 as shown in FIGS. 1-6 includes a body portion 210. As shown, at least a portion of the body portion 210 has a substantially V-shaped footprint (and a corresponding volume with the geometry of a V-shaped prism). The body portion 210 is shown to include a pair of projections 211 extending from opposite sides of the upper portion of the body portion 210 on a first side of the body portion 210. As shown, the projections 211 may form a substantially oblique angle and, as shown in FIGS. 1-6, an acute angle (e.g., based on longitudinal axes extending along the length of each) with one another. In some aspects, the projections 211 may form a substantially orthogonal or obtuse angle. Each of the projections 211 is shown to include at least one opening extending therethrough, where the at least one opening is positioned the same as or similar to that of the opposing projection 211. The one or more openings of the projections 211 may be substantially cylindrical and further may be arranged that a longitudinal axis extending through one or more of the openings may be in a plane substantially perpendicular to that of the longitudinal axes extending along the length of the projections 211. The one or more openings of the projections 211 may be threaded in some embodiments. Further, the one or more openings of the projections 211 may be configured to receive at least a portion of a coupling element at least partially therethrough, for example a set screw or other component configured to releasably and/or movably (e.g., pivotably, translatably, rotatably, etc.) couple multiple components.

The body portion 210 is further shown to include one or more openings 216 arranged on a lower portion of the body portion 210 and extending through the body portion 210 from the first side (e.g., that having the projections 211) to a second side of the body portion 210. The one or more openings 216 may have the same and/or a similar geometry to that of the one or more openings of the projections 211 as shown and described previously herein. For example, the one or more openings 216 may include a threading, geometry, and/or other features configured such that the one or more openings 216 may accommodate a coupling element at least partially therein. In some aspects, said coupling element may include the same and/or similar coupling element to that received at least partially within the one or more openings of the projections 211.

Figure 5:
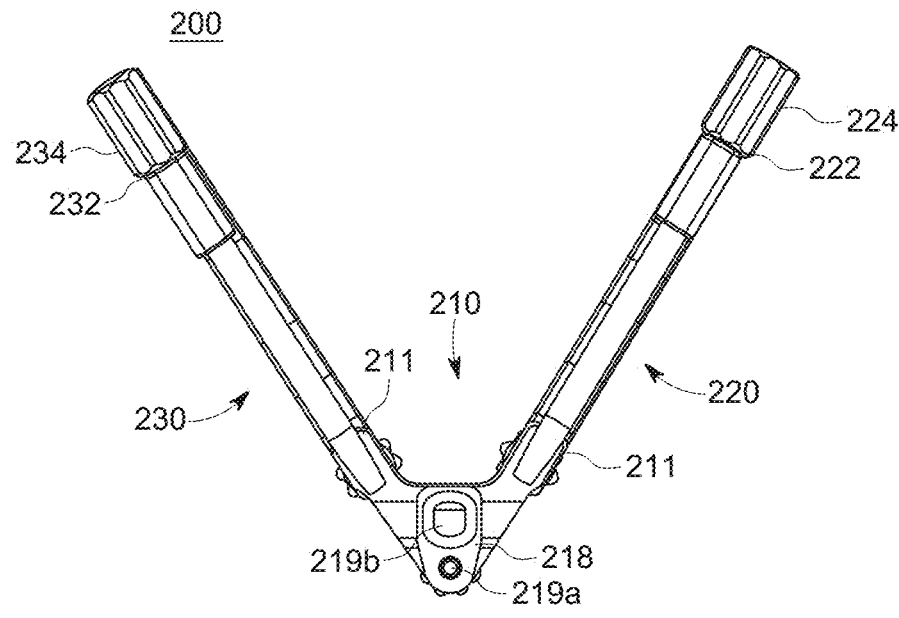
FIG. 5 is a rear view of a portion of the system for aligning and implanting the bone plate, in accordance with the present disclosure.
Figure 6:
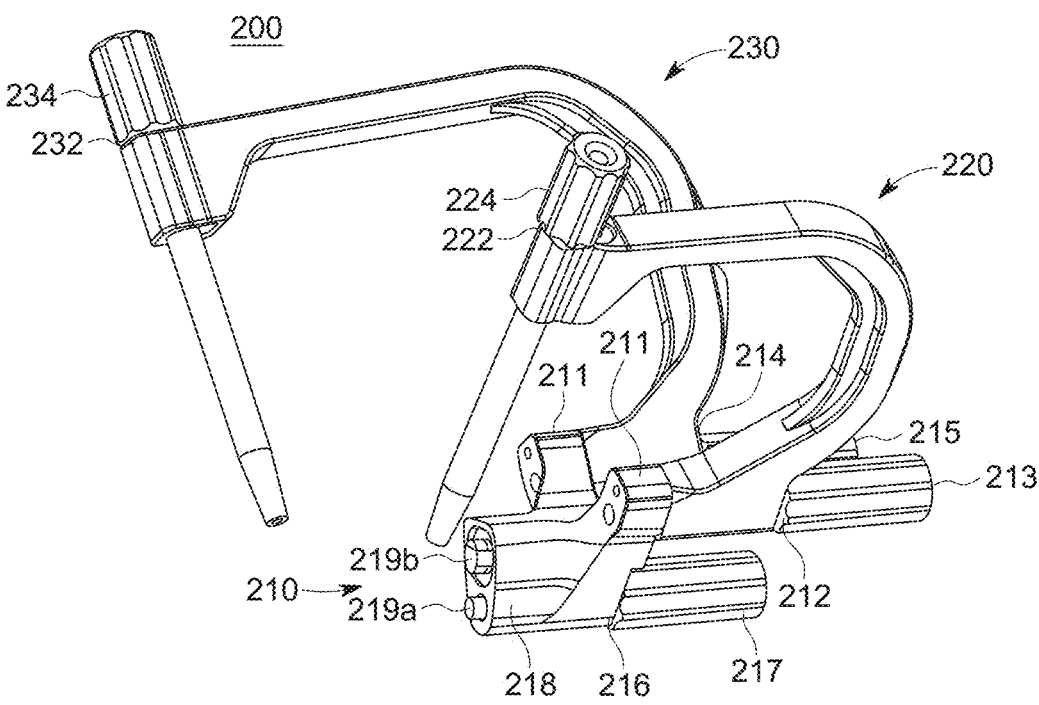
FIG. 6 is a side perspective view of the portion of the system for aligning and implanting the bone plate of FIG. 5, in accordance with the present disclosure.
Figure 7:
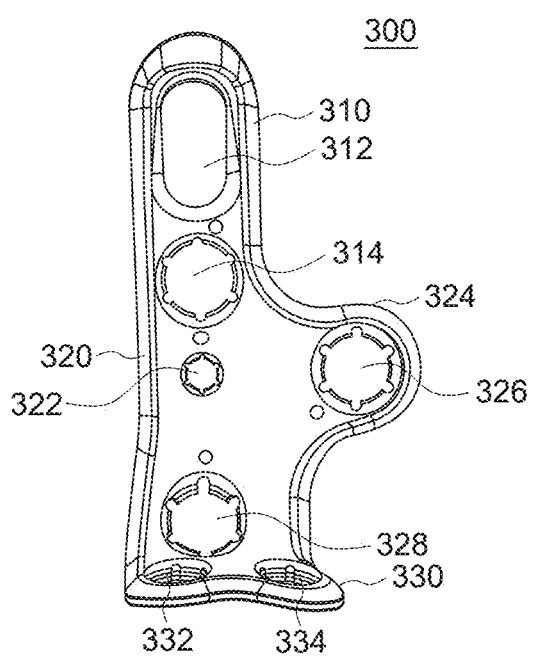
FIG. 7 is a front view of the bone plate shown as a portion of the system for aligning and implanting the bone plate of FIG. 1, in accordance with the present disclosure.

The body portion 210 includes a plate engagement portion 218 arranged on the second side of the body portion 210. The plate engagement portion 218 is shown to protrude from the body portion 210 in a plane substantially orthogonal to that of the projections 211. As shown in FIGS. 5-6, the plate engagement portion 218 includes a lower protrusion 219a arranged substantially below an upper protrusion 219b. With reference to the exemplary embodiment of FIGS. 5-6, the lower and upper projections 219a, 219b have at least partially round geometries. In some aspects, one or both of the lower and upper projections 219a, 219b may include alternate geometries, for example one or more flats arranged about one or more sides of the components. As shown, the lower protrusion 219a has a lesser volume than that of the upper projection 219b, although the volume of the components relative to one another may vary in some embodiments. Further, according to the exemplary embodiment of FIGS. 5-6 the upper projection 219b may be positioned within a depression on a surface of the plate engagement portion 218 (where said surface is opposite the body portion 210 from that on which the one or more openings 216 is positioned). In some aspects, one or more of the lower projection 219a and the upper projection 219b may be resilient, which is to say that one or both components may be compressed at least partially within the plate engagement portion 218 when a force is applied (and return to the protruding position as shown upon release of said force).

One or both of the lower projection 219a and the upper projection 219b may be configured to releasably couple with the plate 300 via one or more engagement features disposed on the plate and configured to accommodate one or both of the lower projection 219a and the upper projection 219b. The coupling element 217 may further manipulate one or both of the lower projection 219a and the upper projection 219b and/or other releasable coupling means between the plate engagement portion 218 and the plate 300 (e.g., the plate may be selectively repositioned, coupled, or decoupled with/from the plate engagement portion 218 by manipulation of the coupling element 217).

The alignment guide 200 is further shown to include a first arm 220 and a second arm 230. The first and second arms 220, 230 are shown to each be releasably (and pivotably) coupled with the one or more openings of the projections 211 by coupling elements 213 and 215, respectively (e.g., a set screw or other coupling element). The first arm 220 includes at least one opening 212 positioned at a first end thereof configured to receive at least a portion of the coupling element 213 therein and therethrough. In some embodiments, the one or more openings 212 may be threaded or have other engagement features therein configured to retain at least a portion of the coupling element 213 and/or otherwise facilitate retention/coupling of the first arm 220 with one of the projections 211 via the coupling element 213. The coupling element 213 is shown to extend at least partially into (and/or therethrough) and be retained within one of the one or more openings 212 and, further, at least partially into (and/or therethrough) one or more of the openings of one of the projections 211. The coupling of the first arm 220 to the projection 211 via the coupling element 213 as shown is a pivotable coupling, with a pivot point for the first arm 220 established about a longitudinal axis running along a length of the coupling element 213 (which, when coupled as shown in FIGS. 1-6, overlays with a longitudinal axis extending through the one of the one or more openings 212 and the opening of the one or more openings of the projection 211 through which at least a portion of the coupling element 213 is received). The first arm 220 is thus pivotable 360-degrees about this pivot point (and, similarly, the second arm 230 is pivotable about such a point of the coupling element 215).

Similarly, the second arm 230 includes at least one opening 214 positioned at a first end thereof configured to receive at least a portion of the coupling element 215 therein and therethrough. In some embodiments, the one or more openings 214 may be threaded or have other engagement features therein configured to retain at least a portion of the coupling element 215 and/or otherwise facilitate retention/coupling of the second arm 230 with one of the projections 211 via the coupling element 215. The coupling element 215 is shown to extend at least partially into (and/or therethrough) and be retained within one of the one or more openings 214 and, further, at least partially into (and/or therethrough) one or more of the openings of one of the projections 211. The coupling of the second arm 230 to the projection 211 via the coupling element 215 as shown is a pivotable coupling, with a pivot point for the second arm 230 established about a longitudinal axis running along a length of the coupling element 215 (which, when coupled as shown in FIGS. 1-6, overlays with a longitudinal axis extending through the one of the one or more openings 214 and the opening of the one or more openings of the projection 211 through which at least a portion of the coupling element 215 is received. It should be noted that, in some aspects, the coupling elements 213, 215 may be identical. Conversely, in some aspects the coupling elements 213, 215 may differ from one another.

The first arm 220 is shown to extend from the one or more openings 212 at the first end of the first arm 220 along a substantially arcuate path having a first length, a transition portion, and a second length terminating in a second end of the first arm 220. As shown, at least portions of the first length and the second length are substantially orthogonal. Further, as shown the first end having the one or more openings 212 has a greater lateral dimension (and volume) than that of the first length, the transition portion, and the second length of the first arm 220. Similarly, the second end arranged opposite the first arm 220 from the first end has a greater lateral dimension (and volume) than that of the second length or the transition portion. The second end of the first arm 220 is shown to include at least one aperture 222 extending from a first surface of the first end through the first end to a second surface of the first end. As shown in the exemplary embodiment of FIGS. 1-6, the at least one aperture 222 includes a pair of apertures arranged adjacent one another and having a substantially cylindrical geometry. The multiple apertures of the one or more apertures 222 as shown may be of different sizes, positions, trajectories, or spacing from other components of the alignment guide 200, or have other specific spatial or geometric parameters. However, in alternate embodiments the at least one aperture 222 may include one or more apertures of various geometries in various positions. Each aperture of the at least one aperture 222 has a longitudinal axis extending therethrough configured in a plane that is oblique to a plane of such a longitudinal axis of the one or more openings 212. As shown, these longitudinal axes may be in planes near orthogonal to one another (or in some aspects, orthogonal to one another).

The one or more apertures 222 of the first arm 220 are shown to receive a guide element 224 extending through one of the one or more apertures 222. The guide element 224 as shown includes a cannulated portion which, when configured as shown in FIGS. 1-6, extends substantially along the longitudinal axis of the aperture of the one or more apertures 222 in which it is received. In practice, the alignment guide 200 may be held static (via fixation to a portion of the anatomy of the patient or otherwise) while a physician manipulates the first arm 220 relative to the other components of the system 100. In some aspects, the physician may insert a stabilization element (e.g., k-wire) through the cannulated portion of the guide element 224 and couple said stabilization element with a portion of the anatomy of a patient (for example, the tibia) such that a distal portion of the guide element is positioned adjacent said portion of the anatomy once a desired position of the first arm 220 has been achieved. Subsequently, in the same procedure (but not necessarily in a step immediately following placement of the stabilization element), the physician may insert other instruments within the cannulated portion of the guide element 224 (with or without the stabilization element remaining therein). For example, the physician may insert a cannulated drill over the stabilization element in order to drill a hole that will ultimately be a path for a fixation element (e.g., a screw) that traverses a joint (e.g., ankle joint, where the drill path goes through the tibia, across the joint space, and into the talus) and is implemented in conjunction with the plate 300 and other components of the system 100.

The second arm 230 is shown to extend from the one or more openings 214 at the first end of the second arm 230 along a substantially arcuate path having a first length, a transition portion, and a second length terminating in a second end of the second arm 230. As shown, at least portions of the first length and the second length are substantially orthogonal. Further, as shown the first end having the one or more openings 214 has a greater lateral dimension (and volume) than that of the first length, the transition portion, and the second length of the second arm 230. Similarly, the second end arranged opposite the second arm 230 from the first end has a greater lateral dimension (and volume) than that of the second length or the transition portion. The second end of the second arm 230 is shown to include at least one aperture 232 extending from a first surface of the first end through the first end to a second surface of the first end. As shown in the exemplary embodiment of FIGS. 1-6, the at least one aperture 232 includes a pair of apertures arranged adjacent one another and having a substantially cylindrical geometry. The multiple apertures of the one or more apertures 222 as shown may be of different sizes, positions, trajectories, spacing from other components of the alignment guide 200, or have other specific spatial or geometric parameters. However, in alternate embodiments the at least one aperture 232 may include one or more apertures of various geometries in various positions. Each aperture of the at least one aperture 232 has a longitudinal axis extending therethrough configured in a plane that is oblique to a plane of such a longitudinal axis of the one or more openings 214. As shown, these longitudinal axes may be in planes near orthogonal to one another (or in some aspects, orthogonal to one another).

The one or more apertures 222 of the second arm 230 are shown to receive a guide element 234 extending through one of the one or more apertures 222. The guide element 234 as shown includes a cannulated portion which as shown in FIGS. 1-6, extends substantially along the longitudinal axis of the aperture of the one or more apertures 222 in which it is received. In practice, the alignment guide 200 may be held static (via fixation to a portion of the anatomy of the patient or otherwise) while a physician manipulates the second arm 230 relative to the other components of the system 100. In some aspects, the physician may insert a stabilization element (e.g., k-wire) through the cannulated portion of the guide element 234 and couple said stabilization element with a portion of the anatomy of a patient (for example, the tibia) such that a distal portion of the guide element is positioned adjacent said portion of the anatomy once a desired position of the second arm 230 has been achieved. Subsequently in the same procedure (but not necessarily in a step immediately following the placement of the stabilization element), the physician may insert other instruments within the cannulated portion of the guide element 234 (with or without the stabilization element remaining therein). For example, the physician may insert a cannulated drill over the stabilization element in order to drill a hole that will ultimately be a path for a fixation element (e.g., a screw) that traverses a joint (e.g., ankle joint, where the drill path goes through the tibia, across the joint space, and into the talus) and is implemented in conjunction with the plate 300 and other components of the system 100. As shown, the first and second arms 220, 230 are identical to one another. However, it should be understood that in some aspects the first arm 220 may differ from the second arm 230 in size, geometry, shape, couplability, or other aspects.

Figure 8:
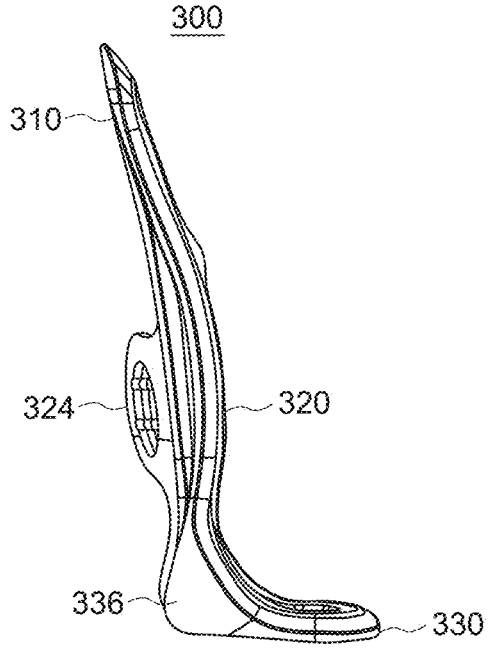
FIG. 8 is a right side view of the bone plate shown as a portion of the system for aligning and implanting the bone plate of FIG. 1, in accordance with the present disclosure.
Figure 9:
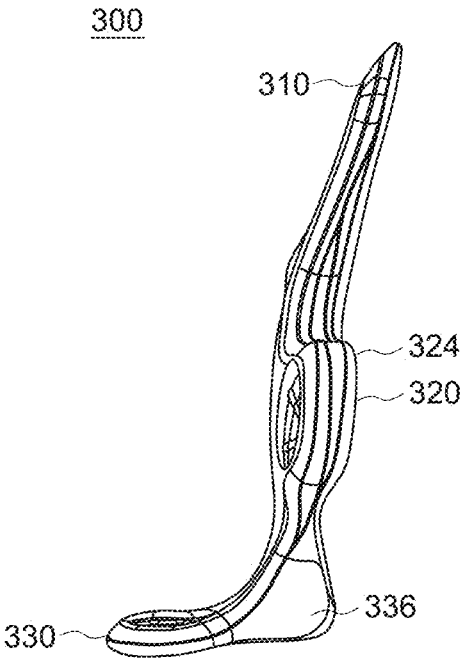
FIG. 9 is a left side view of the bone plate shown as a portion of the system for aligning and implanting the bone plate of FIG. 1, in accordance with the present disclosure.
Figure 10:
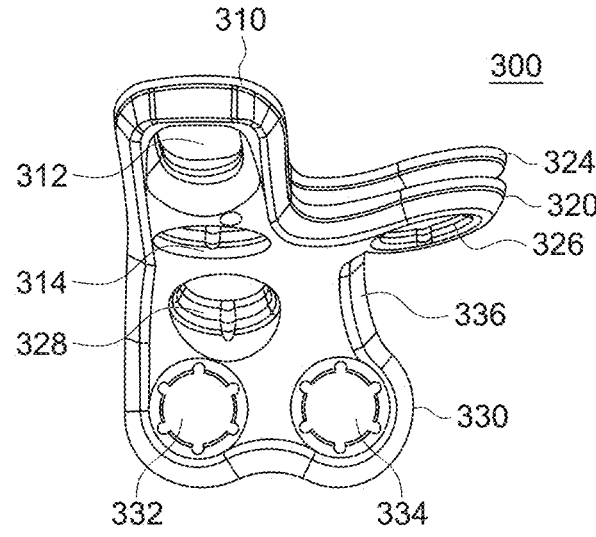
FIG. 10 is a top view of the bone plate shown as a portion of the system for aligning and implanting the bone plate of FIG. 1, in accordance with the present disclosure.
Figure 11:
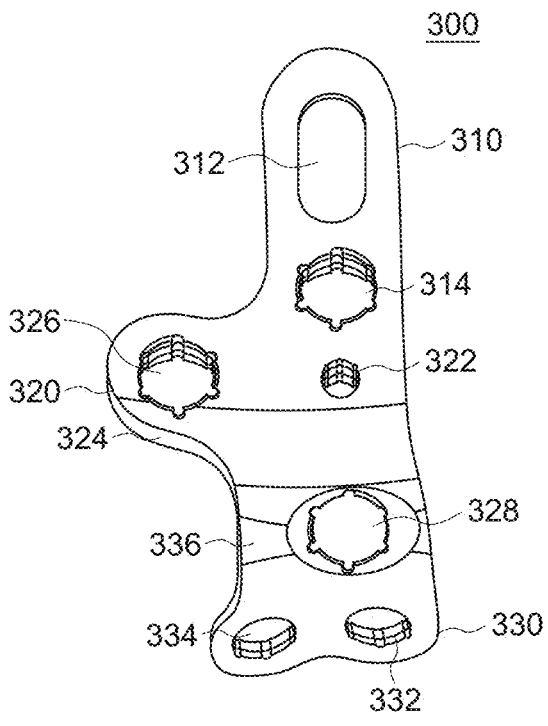
FIG. 11 is a rear view of the bone plate shown as a portion of the system for aligning and implanting the bone plate of FIG. 1, in accordance with the present disclosure.
Figure 12:
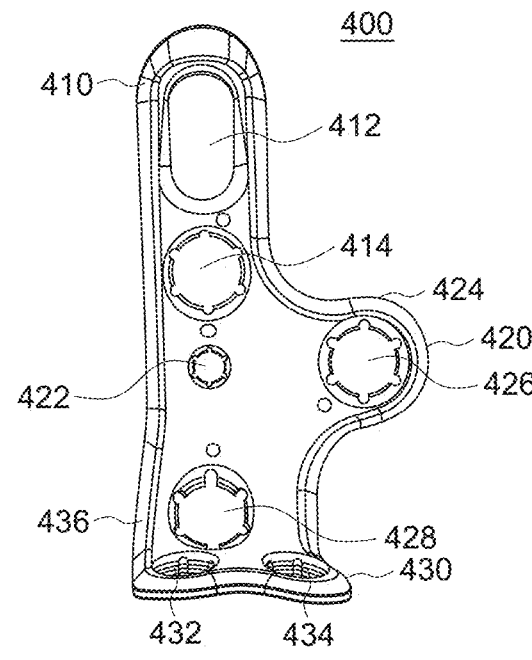
FIG. 12 is a front view of an alternate bone plate that may be implemented with the system for aligning and implanting the bone plate of FIG. 1, in accordance with the present disclosure.

The plate 300 is shown to include an upper portion 310, a central portion 320, and a lower portion 330. The plate 300 further includes a first side (e.g., shown in FIG. 7) and a second side (e.g., shown in FIG. 11). The first side may include one or more markings identifying size, configuration, directionality (e.g., left/right) or other implant specific information. The second side may be configured to interface directly with a bone surface of one or more bones of a patient (e.g., the tibia and the talus). As shown, the lower portion 330 is offset from the central portion 320, for example as shown in FIGS. 8 and 9 at a substantially orthogonal angle (although this angle may also be oblique). With reference to FIGS. 8 and 9, the second surface of the plate 300 is substantially flat (e.g., lies in one plane along the upper and central portions), whereas the first surface of the plate 300 has a curvature extending at least partially away from the second surface. With continued reference to FIGS. 8 and 9, in some embodiments different portions of the plate 300 may have different thicknesses (e.g., dimension between first and second sides) in the upper, central, and lower portions 310, 320, and 330, respectively. For example, the upper portion 310 may have a lesser thickness than at least a portion of the central portion 320 and the lower portion 330 and vice-a versa.

The upper portion 310 includes a protrusion from the central portion 320 and is shown to include a slot 312 extending vertically along a portion of the length of the upper portion 310 of the plate 300. As shown, the slot 312 has a greater vertical dimension than lateral dimension and when the plate 300 is used by a physician, may receive a fastener (e.g., screw) therethrough. Further, the slot 312 may be used by a physician as an adjustable slot (e.g., once a screw is inserted therethrough thus coupling the plate 300 with a bone of a patient the plate 300 may still be manipulated as allowed by the fastener within the dimensions of the slot 312. In some aspects, the slot 312 may have sloped portions (e.g., changes in elevation between the first and second surfaces) to facilitate the aforementioned compression such that a physician may place a fastener at an oblique trajectory therethrough and thus apply compression across a joint spanned by the plate 300. The upper portion 310 is further shown to include an opening 314 configured to receive a fastener therethrough to facilitate coupling of the plate 300 with a portion of a bone of a patient.

The central portion 320 of the plate 300 is disposed substantially between the upper portion 310 and the lower portion 330 and is shown to include a protuberance 324 extending laterally therefrom. As shown, the protuberance 324 has a rounded geometry and a longitudinal axis thereof extends substantially orthogonal to such an axis running along the vertical dimension of the plate (e.g., bisecting the slot 312). The protuberance 324 includes an opening 326 configured to receive a fastener so as to facilitate coupling with a portion of a bone of a patient. The central portion 320 also includes an opening 322 with a smaller diameter than that of the opening 326, where the opening 322 is configured to facilitate releasable coupling with the plate engagement portion 218 of the alignment guide 200 via the lower projection 219a and/or the upper projection 219b. For example, one of the lower projection 219a and the upper projection 219b may be received within the opening 322 so as to releasably couple the plate 300 to the alignment guide 200 such that the plate 300 may be manipulated by components of the alignment guide 200 (e.g., rotated, etc.). The central portion 320 of the plate 300 may also include additional openings configured to facilitate placement, manipulation, and releasable coupling of the plate 300 with instrumentation (e.g., alignment guide 200) or portions of the anatomy of the patient. Additionally, the central portion 320 of the plate 300 may include various markings, for example product numbers, sizing, and other identifying information for the plate 300.

The lower portion 330 of the plate 300 is shown to extend from the central portion 320 such that the first surface of the central portion 320 forms an angle with the first surface of the lower portion 330. As shown, this angle may be substantially orthogonal, but may also be oblique in some embodiments. The plate 300 is shown to include an opening 328 configured between the central portion 320 and the lower portion 330 (e.g., at a transition portion 336 disposed between the central portion 320 and the lower portion 330) such that portions of the area of the opening 328 are arranged on both the central and lower portions 320, 330 (or, for example, on the transition portion 336 which may have a substantially curved, rounded, concave, or convex geometry) of the plate 300. As shown, many of the openings on the plate 300 extend through the plate 300 and have longitudinal axes substantially orthogonal to the first and second surfaces of the plate 300. The opening 328 has a longitudinal axis that extends at an oblique angle relative to the first and second surfaces of the central portion 320 and the lower portion 330 as shown in the exemplary embodiment of FIGS. 7-11. The lower portion 330 of the plate 300 further includes a pair of openings 332 and 334 arranged adjacent to one another. The openings 332, 334 are configured to receive fasteners therethrough and facilitate coupling with a portion of a bone of a patient (e.g., a talus).

Figure 13:
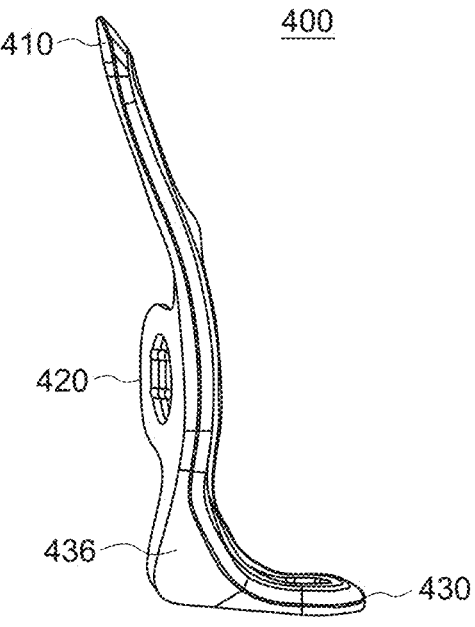
FIG. 13 is a right side view of the alternate bone plate of FIG. 12 that may be implemented with the system for aligning and implanting the bone plate of FIG. 1, in accordance with the present disclosure.
Figure 14:
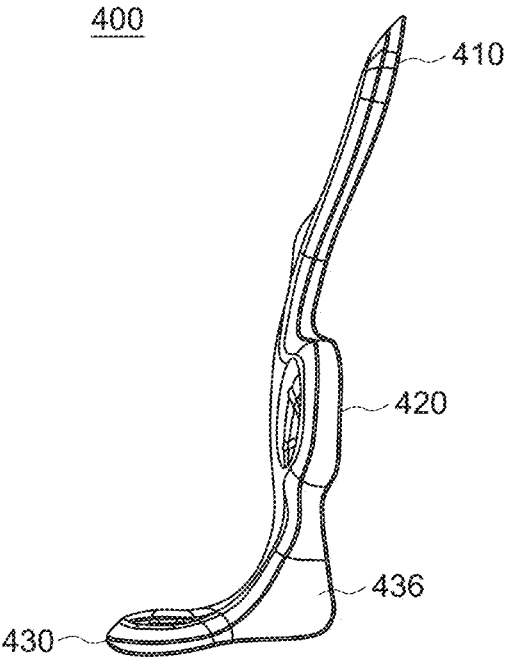
FIG. 14 is a left side view of the alternate bone plate of FIG. 12 that may be implemented with the system for aligning and implanting the bone plate of FIG. 1, in accordance with the present disclosure.
Figure 15:
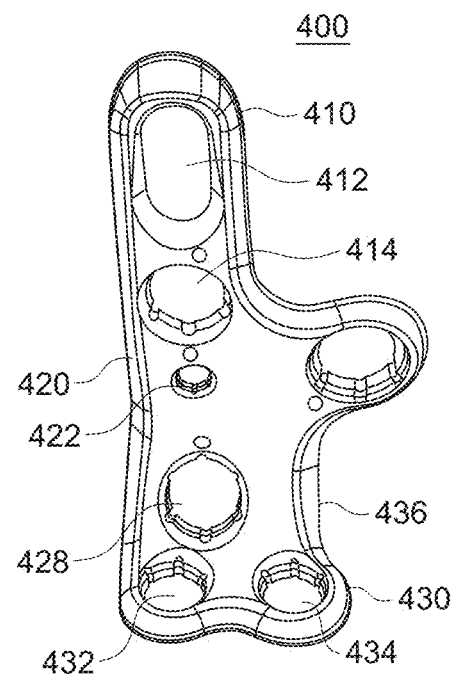
FIG. 15 is a front, top perspective view of the alternate bone plate of FIG. 12 that may be implemented with the system for aligning and implanting the bone plate of FIG. 1, in accordance with the present disclosure.
Figure 16:
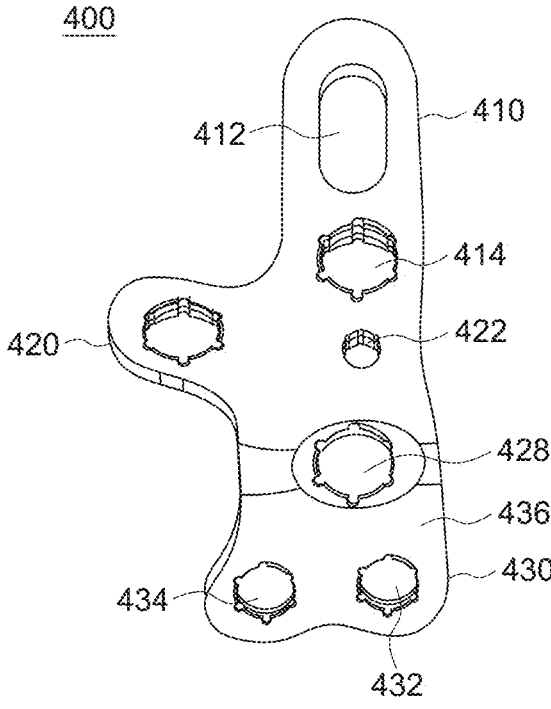
FIG. 16 is a bottom view of the alternate bone plate of FIG. 12 that may be implemented with the system for aligning and implanting the bone plate of FIG. 1, in accordance with the present disclosure.

Referring now to FIGS. 12-16, another plate 400 is shown. The plate 400 as shown has a similar geometry and components to the plate 300 as shown and described herein. Further, the plate 400 may be provided (e.g., sold, etc.) in a system including the alignment guide 200 (where the plate 400 is compatible with the alignment guide 200 in the same manner as the plate 300). The plate 400 is shown to include an upper portion 410, a central portion 420, and a lower portion 430. The plate 400 further includes a first side (e.g., shown in FIG. 12) and a second side (e.g., shown in FIG. 16). The first side may include one or more markings identifying size, configuration, directionality (e.g., left/right) or other plate specific information. The second side may be configured to interface directly with a bone surface of one or more bones of the patient (e.g., the tibia and the talus). As shown, the lower portion 430 is offset from the central portion 420, for example as shown in FIGS. 13-14 at a substantially orthogonal angle (although this angle may also be oblique). With reference to FIGS. 13 and 14, the second surface of the plate 400 is substantially contoured (e.g., does not lie in one plane along the upper and central portions), and is complimentary to the first surface of the plate 400, which has a curvature. The curvature of the second surface of the plate 400 may be configured to contour to one or more portions of one or more bones of a patient (for example, the upper portion 410 of the plate 400 (and to a lesser degree, upper portion 310 of the plate 300) extends from the central portion 420 at an oblique angle when viewed as shown in FIGS. 13 and 14). With continued reference to FIGS. 13 and 14, in some embodiments different portions of the plate 400 may have different thicknesses (e.g., dimension between first and second sides) in the upper, central, and lower portions 410, 420, and 430, respectively. For example, the upper portion 410 may have a lesser thickness than at least a portion of the central portion 420 and the lower portion 430 and vice-a versa.

The upper portion 410 includes a protrusion 424 from the central portion 420 and is shown to include a slot 412 extending vertically along a portion of the length of the upper portion 410 of the plate 400. As shown, the slot 412 has a greater vertical dimension than lateral dimension and when the plate 400 is used by the physician, may receive a fastener (e.g., screw) therethrough. Further, the slot 412 may be used by the physician as an adjustable slot (e.g., once a screw is inserted therethrough thus coupling the plate 400 with a bone of the patient the plate 400 may still be manipulated as allowed by the fastener within the dimensions of the slot 412. In some aspects, the slot 412 may have sloped portions (e.g., changes in elevation between the first and second surfaces) to facilitate the aforementioned compression such that the physician may place a fastener at an oblique trajectory therethrough and thus apply compression across a joint spanned by the plate 400. The upper portion 410 is further shown to include an opening 414 configured to receive a fastener therethrough to facilitate coupling of the plate 400 with a portion of the bone of the patient.

The central portion 420 of the plate 400 is disposed substantially between the upper portion 410 and the lower portion 430 and is shown to include a protuberance 424 extending laterally therefrom. As shown, the protuberance 424 has a rounded geometry and a longitudinal axis thereof and extends substantially orthogonal to such an axis running along the vertical dimension of the plate (e.g., bisecting the slot 412). The protuberance 424 includes an opening 426 configured to receive a fastener so as to facilitate coupling with a portion of a bone of the patient. The central portion 420 also includes an opening 422 with a smaller diameter than that of the opening 426, where the opening 422 is configured to facilitate releasable coupling with the plate engagement portion 218 of the alignment guide 200 via the lower projection 219*a* and/or the upper projection 219*b*. For example, one of the lower projection 219*a* and the upper projection 219*b* may be received within the opening 422 so as to releasably couple the plate 400 to the alignment guide 200 such that the plate 400 may be manipulated by components of the alignment guide 200 (e.g., rotated, etc.). The central portion 420 of the plate 400 may also include additional openings configured to facilitate placement, manipulation, and releasable coupling of the plate 400 with instrumentation (e.g., alignment guide 200) or portions of the anatomy of the patient. Additionally, the central portion 420 of the plate 400 may include various markings, for example product numbers, sizing, and other identifying information for the plate 400.

The lower portion 430 of the plate 400 is shown to extend from the central portion 420 such that the first surface of the central portion 420 forms an angle with the first surface of the lower portion 430. As shown, this angle may be substantially orthogonal but may also be oblique in some embodiments. The plate 400 is shown to include an opening 428 configured between the central portion 420 and the lower portion 430 (e.g., at a transition portion 336 disposed between the central portion 320 and the lower portion 330) such that portions of the area of the opening 428 are arranged on both the central and lower portions 420, 430 (or, for example, on the transition portion 436 which may have a substantially curved, rounded, concave, or convex geometry) of the plate 400. As shown, many of the openings on the plate 400 extend through the plate 400 and have longitudinal axes substantially orthogonal to the first and second surfaces of the plate 400. The opening 428 has a longitudinal axis that extends at an oblique angle relative to the first and second surfaces of the central portion 420 and the lower portion 430 as shown in the exemplary embodiment of FIGS. 12-16. The lower portion 430 of the plate 400 further includes a pair of openings 432, 434 arranged adjacent one another. The openings 432, 434 are configured to receive fasteners therethrough and facilitate coupling with a portion of a bone of a patient (e.g., a talus).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A bone plate alignment system, comprising:
an alignment guide, comprising:
a body portion, comprising:
a first projection extending away from an upper portion of the body portion in a first direction;
a second projection extending away from the upper portion of the body portion in a second direction opposite the first direction; and
a plate engagement portion extending away from a posterior surface of the body portion;
a first arm extending from a first side of the body portion; and
a second arm extending from a second side of the body portion; and
a bone plate, comprising:
an upper portion;
a lower portion; and
an intermediate portion disposed between the upper and lower portions.

2. The system of claim 1, wherein the first and second arms extend from the first and second projections of the body portion at a substantially oblique or orthogonal angle relative to one another.

3. The system of claim 2, wherein the first arm comprises a first opening at a first end thereof and the second arm comprises a second opening at a first end thereof.

4. The system of claim 3, wherein the first arm comprises a third opening at a second end thereof and the second arm comprises a fourth opening at a second end thereof.

5. The system of claim 4, wherein each of the first and second arms extend along an arcuate path comprising a transition portion between the first and second ends thereof.

6. The system of claim 5, wherein at least one of the first and second arms is pivotable relative to at least a portion of the body portion.

7. The system of claim 6, wherein the first opening comprises a first longitudinal axis extending therethrough and the third opening comprises a third longitudinal axis extending therethrough, and wherein the first and third longitudinal axes are disposed in planes which are substantially orthogonal to one another.

8. The system of claim 7, wherein the second opening comprises a second longitudinal axis extending therethrough and the fourth opening comprises a fourth longitudinal axis extending therethrough, and wherein the second and fourth longitudinal axes are disposed in planes which are substantially orthogonal to one another.

9. The system of claim 8, wherein each of the first, second, third, and fourth openings are configured to receive a guide element therein.

10. The system of claim 9, wherein the guide element is cannulated.

11. The system of claim 1, wherein the plate engagement portion, comprises:

an upper projection; and a lower projection.

12. The system of claim 1, wherein the upper portion of the bone plate comprises at least one opening configured to receive at least one fastener to facilitate coupling with a first bone.

13. The system of claim 12, wherein the lower portion of the bone plate comprises at least one opening configured to receive at least one fastener to facilitate coupling with a second bone.

14. The system of claim 13, wherein the lower portion of the bone plate is offset from the upper portion at a substantially orthogonal angle.

15. The system of claim 13, wherein the lower portion of the bone plate is offset from the upper portion at a substantially oblique angle.

16. The system of claim 13, wherein the intermediate portion of the bone plate comprises a protuberance extending laterally therefrom, and wherein the protuberance comprises a substantially rounded geometry and comprises an opening extending therethrough.

17. The system of claim 16, wherein the bone plate comprises a transition portion disposed between the intermediate and lower portions of the bone plate, wherein the transition portion comprises a curved geometry and at least one opening.

18. The system of claim 17, wherein the upper portion of the bone plate comprises at least one slot, the intermediate portion of the bone plate comprises at least one opening extending therethrough, and the lower portion of the bone plate comprises at least one opening extending therethrough.

19. A bone plate alignment system, comprising:

an alignment guide, comprising:

a body portion, comprising:

a first projection extending away from an upper portion of the body portion in a first direction; and a second projection extending away from the upper portion of the body portion in a second direction opposite the first direction, wherein the first projection and the second projection form a V-shape as the first and second projections extend away from the body portion;

a first arm extending from a first side of the body portion and comprising an arcuate geometry; and a second arm extending from a second side of the body portion and comprising an arcuate geometry, wherein the first and second arms are pivotably coupled with the body portion and are pivotable relative to at least a portion of the body portion; and a bone plate, comprising:

an upper portion comprising at least one slot; and a lower portion comprising at least one opening, wherein the upper and lower portions are offset from one another at a substantially orthogonal angle.

20. A bone plate alignment system, comprising:

an alignment guide, comprising:

a body portion, comprising:

a first projection extending away from an upper portion of the body portion in a first direction; and a second projection extending away from the upper portion of the body portion in a second direction opposite the first direction;

a first arm pivotably coupled with and extending from the first projection on a first side of the body portion; and a second arm pivotably coupled with and extending from the second projection on a second side of the body portion; and a bone plate, comprising:

an upper portion comprising at least one slot extending therethrough;

a lower portion offset from the upper portion and comprising at least one opening extending therethrough; and an intermediate portion disposed between the upper and lower portions, comprising:

at least one opening; and at least one protuberance extending laterally therefrom and comprising at least one opening extending therethrough.

* * * * *